(12) United States Patent
Sato

(10) Patent No.: US 6,522,718 B2
(45) Date of Patent: Feb. 18, 2003

(54) X-RAY FLUORESCENCE THICKNESS TESTER

(75) Inventor: Masao Sato, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/903,236

(22) Filed: Jul. 12, 2001

(65) Prior Publication Data

US 2002/0025020 A1 Feb. 28, 2002

(30) Foreign Application Priority Data

Jul. 18, 2000 (JP) ........................... 2002-217046

(51) Int. Cl.[7] ............................................. G01N 23/223
(52) U.S. Cl. ............................ 378/50; 378/44; 378/45; 378/46
(58) Field of Search ..................... 378/44, 45, 46, 378/49, 50, 70, 72, 76, 84, 86, 88, 89, 90

(56) References Cited

U.S. PATENT DOCUMENTS

| | | | | |
|---|---|---|---|---|
| 5,299,252 A | * | 3/1994 | Takahashi | 378/50 |
| 5,457,725 A | * | 10/1995 | Sato | 378/44 |
| 5,778,039 A | * | 7/1998 | Hossain et al. | 378/45 |
| 5,926,522 A | * | 7/1999 | McCarthy et al. | 378/84 |
| 5,937,026 A | * | 8/1999 | Satoh | 378/44 |
| 6,108,398 A | * | 8/2000 | Mazor et al. | 378/45 |
| 6,292,532 B1 | * | 9/2001 | Kawahara et al. | 378/49 |
| 6,426,993 B1 | * | 7/2002 | Satoh | 378/45 |

OTHER PUBLICATIONS

Huber et al., Nuclear Instruments and Methods in Physics Research B 99, 665 (1995).*

* cited by examiner

Primary Examiner—Robert H. Kim
Assistant Examiner—Allen C. Ho
(74) Attorney, Agent, or Firm—Adams & Wilks

(57) ABSTRACT

In order to realize accurate measurement with an X-ray fluorescence thickness tester characterized by being non-destructive and non-contacting, a system comprises an X-ray generating source, a collimator for focusing primary X-rays, and a sample observation optical system for positioning and observation of microscopic sections. As thickness testing means, as detectors for detecting X-ray fluorescence generated from the sample there is one sensor having low counting efficiency but excellent energy resolution used for low energy counting, and another sensor having poor energy resolution but excellent counting efficiency used for counting high energy, these two sensors being arranged next to each other, and in stages subsequent to the detector preamps there are separate linear amps and frequency analyzers with respective signals being subjected to processing as spectrums for qualitative and quantitative analysis in a common control and computing section.

2 Claims, 2 Drawing Sheets

X-RAY FLUORESCENCE THICKNESS TESTER

BACKGROUND OF THE INVENTION

The present invention relates to an energy dispersive X-ray fluorescence thickness tester having the merits of multiple simultaneous elements and non-destructiveness used in thickness control in the surface treatment industry, such as plating or sputtering films.

Conventionally, with an energy dispersive X-ray fluorescence thickness tester, film formation for surface treatment is well known and used in a production line for the purpose of quality control. This means that there is a limitation that there is no time for measurement. Further, high counting efficiency becomes important due to the energy distribution, X-ray fluorescence thickness testers using a proportional counter are mainstream, and in the case of use for the purpose of research and development, accuracy and sensitivity are required due to the limitations with respect to measurement time, and X-ray fluorescence thickness testers fitted with Si (Li) semiconductor detectors having excellent energy resolution or PIN diode X-ray detectors are also used.

In an energy dispersive detector, regarding detection performance, resolution and counting efficiency are mutually incompatible. This means that generally if width and area of a sensor device is enlarged in order to improve counting efficiency, then resolution is impaired or no longer functions.

Conventionally, in the case of performing film thickness measurement with an X-ray fluorescence thickness tester, since a proportional counter is generally used, if there is separation to the extent of the atomic number of elements constituting a thin film or a material (substrate), accurate composite measurement is possible even without carrying out specialized processing, but nickel (z=28) and copper (z=29) that have atomic numbers next to each other in the periodic table of elements are separated, and are overlaid in order to count respective peaks. This means that either a secondary filter method is used to insert a cobalt (Z=27) thin plate in front of the detector to perform peak separation using a difference in absorption effect in the cobalt with respect to nickel and copper, or a digital filter method is used to mathematically perform peak separation from peak shapes. However, the secondary filter method is restricted in application combinations. If there is a dedicated machine then the secondary filter method is effective, but if the purpose is to measure various combinations this method can not be used. Also, the digital filter method can be applied to various combinations, but there is a problem with stability compared with the secondary filter method, accompanying peak separation errors.

If there are requirements for peak separation, it is possible to use an Si (Li) semiconductor detector having excellent energy resolution, but in order to use an Si (Li) semiconductor detector it is necessary to periodically supply liquid nitrogen as a cooling medium, and there is a problem with respect to cost and operability. Also, in order to solve the problem of liquid nitrogen supply, a PIN detector is adopted that degrades energy resolution but can be used with Peltier cooling. In this case, detection efficiency with respect to high energy X-rays is poor in principle, and this method is limited to low energy X-ray applications.

SUMMARY OF THE INVENTION

In low energy regions in the vicinity of X-ray energy, a PIN detector having excellent energy resolution is used, and in high energy regions where counting efficiency of a PIN detector is low, a proportional counter or CdZnTe detector having poor resolution but excellent counting efficiency is used, since there is no need for resolution.

DETAILED DESCRIPTION OF THE PREFERRED EMBODIMENT

Figure 1:
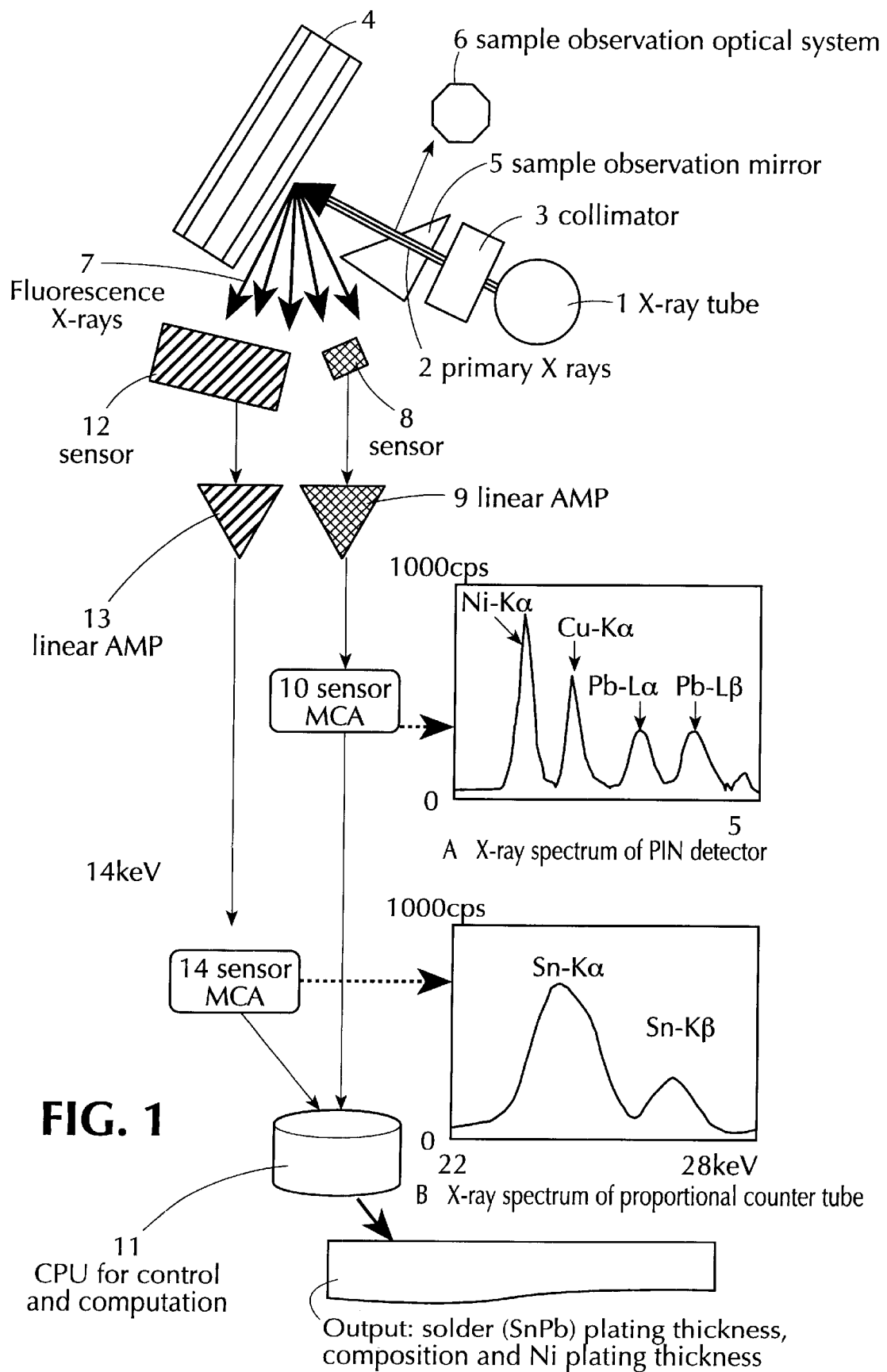
FIG. 1 is a drawing showing energy dispersive X-ray fluorescence.

FIG. 1 shows an embodiment of an energy dispersive X-ray fluorescence thickness tester fitted with two types of detector enabling processing for simultaneously detecting a high resolution X-ray spectrum and a low counting efficiency X-ray spectrum.

A sample 4 is irradiated using means 3 for focusing primary X-rays 2 irradiated from an X-ray tube 1 into microscopic sections with a slit, a collimator or a capillary or a total reflection phenomenon.

At the time of irradiation, since measurement regions are microscopic, a sample observation mirror 5 and a sample observation optical system 6 are provided for positioning of the measurement locations. X-ray fluorescence 7 generated from the sample is arranged so as to be detected by the energy dispersive first sensor 8 and second sensor 12. As an energy dispersive X-ray detector, a sensor 8 characterized by high resolution, for example a PIN diode detector or a high resolution X-ray detector such as a silicon drift chamber, is provided. In the case where a PIN diode detector is adopted as the sensor 8, resolution (FWHM) for a Mn-K$\alpha$ line (5.9 keV) is around 200 eV, which is a relatively high resolution and counting efficiency is at a level from 10,000–20,000 cps which is a relatively low counting efficiency. However, since the high energy X-ray detection efficiency is poor, it acts as a low energy detector. If a proportional counter is adopted as the sensor 12, resolution is around 1 keV, which is a relativity low resolution while there is a possibility that counting efficiency will become a level of a few tens of thousand cps, which is a relatively high counting efficiency, while in the case of using a scintillation counter, resolution is as poor as a few keV it is possible to obtain a counting efficiency of hundreds of thousands of cps. In the high energy region, since there is less overlapping of X-rays there is no need for resolution and high energy detection efficiency is also good, which means that it acts as a high energy detector.

In the case of adopting a CdZnTe detector, since this has the same probe shape as the PIN diode detector there is the advantage that it can be arranged without being subject to space limitations.

With this embodiment, stages after the respective detector preamps are made up of respective linear AMPs 9 and 13, and spectrum analyzers (MCA) 10 and 14, with respective signals being quantitatively processed in CPU 11 for control and computation, but it is also possible for stages after the respective detectors to be a single digital circuit.

With this embodiment, an example of two X-ray spectrums A and B is shown for the case where the sample 4 is solder plating on nickel plating on copper, with an X-ray spectrum for a Ni-K$\alpha$ line (7.47 keV), a Cu-K$\alpha$ line (8.04 keV) and a Pb-L $\alpha$ line (10.55 keV) being counted by the sensor 8, while a Sn-K $\alpha$ line (25.19 keV) is counted by sensor 12.

Figure 2:
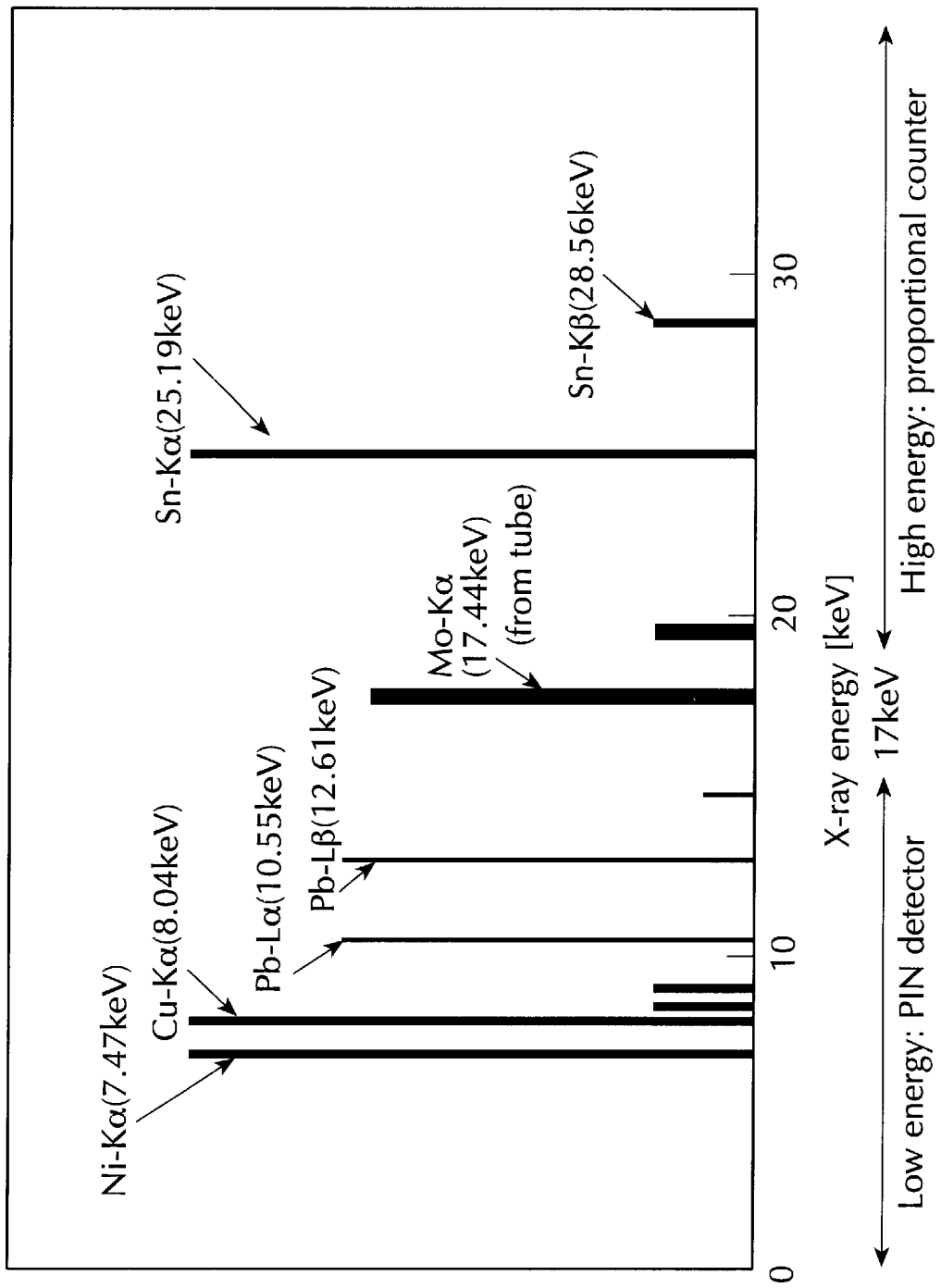
FIG. 2 is a drawing showing an X-ray energy relationship and a counting range of the respective counters.

With respect to division of the detection energy regions, since in this embodiment, for example, a molybdenum target is used in an X-ray tube, as shown in FIG. 2, with a Mo-K$\alpha$ as a criterion below 17 keV is low energy and a PIN detector is used, and if 17 keV is exceeded a proportional counter is used. The resolution of a CdZnTe makes it possible to construct a system that is much better than a proportional counter.

The present invention enables efficient and accurate measurement from low energy to high energy using X-ray fluorescence, at high resolution, without the need for high sensitivity, or liquid nitrogen.

What is claimed is:

1. An X-ray fluorescence thickness tester, provided with an X-ray generating system made up of a high voltage power source and an X-ray tube, means for focusing primary X-rays irradiated from the X-ray generating system onto microscopic sections with a slit, a collimator or a capillary utilizing a total reflection phenomenon, and a sample observation optical system for positioning used in measurement of microscopic measurement regions, comprising:

a liquid nitrogen-less PIN diode X-ray detector or a silicon drift chamber used as a first sensor with low counting efficiency but high energy resolution, for detecting X-ray fluorescence generated from an object sample, and a proportional counter, CdZnTe detector or a scintillation counter as a second sensor having low energy resolution but high counting efficiency for high energy compared to the first sensor, arranged side by side in a sample chamber that is open to the atmosphere and not evacuated, wherein a system is divided between the two sensors according to energy of X-ray fluorescence, by adopting the first sensor for X-ray fluorescence from low energy, and adopting the second sensor for X-ray fluorescence from high energy, and stages subsequent to each of the detectors are made up of a separate preamp, linear amp, and frequency analyzer, and quantitative processing is carried out in common control and computing sections.

2. An X-ray fluorescence thickness tester, provided with an X-ray generating system made up of a high voltage power source and an X-ray tube, means for focusing primary X-rays irradiated from the X-ray generating system onto microscopic sections with a slit, a collimator or a capillary utilizing a total reflection phenomenon, and a sample observation optical system for positioning used in measurement of microscopic measurement regions, comprising:

a liquid nitrogen-less PIN diode X-ray detector or a silicon drift chamber used as a first sensor with low counting efficiency but high energy resolution, for detecting X-ray fluorescence generated from an object sample, and a proportional counter, CdZnTe detector or a scintillation counter as a second sensor having low energy resolution but high counting efficiency for high energy compared to the first sensor, arranged side by side in a sample chamber that is open to the atmosphere and not evacuated, wherein a system is divided between the two sensors according to energy of X-ray fluorescence, by adopting the first sensor for x-ray fluorescence from low energy, and adopting the second sensor for X-ray fluorescence from high energy, and stages subsequent to each of the detectors are divided up to a separate preamp, functions of a linear amp and frequency analyzer are grouped together in a single digital circuit, and quantitative processing is carried out in common control and computing sections.

* * * * *